(12) United States Patent
Ellis et al.

(10) Patent No.: US 12,351,820 B2
(45) Date of Patent: *__Jul. 8, 2025__

(54) METHODS FOR CULTURING ORGANOIDS

(71) Applicant: CELLESCE LIMITED, Caerdydd (GB)

(72) Inventors: Marianne J. Ellis, Caerdydd (GB);
Julian Chaudhuri, Caerdydd (GB);
Trevor Clive Dale, Caerdydd (GB)

(73) Assignee: Molecular Devices (UK) Limited, Wokingham (GB)

( * ) Notice: Subject to any disclaimer, the term of this patent is extended or adjusted under 35 U.S.C. 154(b) by 0 days.

This patent is subject to a terminal disclaimer.

(21) Appl. No.: 17/858,920

(22) Filed: Jul. 6, 2022

(65) Prior Publication Data

US 2022/0333064 A1 Oct. 20, 2022

Related U.S. Application Data

(63) Continuation of application No. 16/316,573, filed as application No. PCT/GB2017/052026 on Jul. 11, 2017, now Pat. No. 11,401,501.

(30) Foreign Application Priority Data

Jul. 11, 2016 (GB) ..................................... 1611982

(51) Int. Cl.
*C12N 5/00* (2006.01)
*C12N 5/071* (2010.01)

(52) U.S. Cl.
CPC ......... *C12N 5/0081* (2013.01); *C12N 5/0062* (2013.01); *C12N 5/0679* (2013.01); *C12N 2509/10* (2013.01); *C12N 2513/00* (2013.01); *C12N 2533/00* (2013.01); *C12N 2533/50* (2013.01)

(58) Field of Classification Search
CPC ... C12N 5/0081; C12N 5/0062; C12N 5/0679
See application file for complete search history.

(56) References Cited

U.S. PATENT DOCUMENTS

| 4,816,395 | A | 3/1989 | Hancock et al. | |
| 4,937,182 | A | 6/1990 | Hancock et al. | |
| 8,252,591 | B2 | 8/2012 | Ince et al. | |
| 10,597,633 | B2 * | 3/2020 | Huch Ortega | C12N 5/0602 |
| 2014/0030762 | A1 * | 1/2014 | Deplano | C12M 41/44 435/397 |

FOREIGN PATENT DOCUMENTS

| GB | 2532814 | A | 6/2016 |
| JP | 2014233209 | A | 12/2014 |
| WO | 2004013315 | A1 | 2/2004 |
| WO | 2007094511 | A1 | 8/2007 |
| WO | 2009023194 | A2 | 4/2009 |
| WO | 2012100084 | A1 | 7/2012 |
| WO | 2012143407 | A1 | 10/2012 |
| WO | 2013063588 | A1 | 5/2013 |
| WO | 2016083612 | A1 | 6/2016 |

OTHER PUBLICATIONS

Pierzchalska et al., BioTechniques, 2012, 52:307-315.*
Catapano, Cell and Tissue Reaction Engineering: Principles and Practice, 2009, Chapter 7: 279-313.*
Lancaster, M. A.; Knoblich, J. A. 'Organogenesis in a dish: Modeling development and disease using organoid technologies. (2014) Science, 345, 1247125, 1-9.
Drioli, E.; Bartolo, L. D. "Membrane bioreactor for cell tissues and organoids." Artificial Organs (2006), 30(10); p. 793-802.
Miyoshi, H.; Stappenbeck, T. S. "In vitro expansion and genetic modification of gastrointestinal stem cells in spheroid culture." Nature Protocols, (2013), vol. 8, No. 12, p. 2471-2482.
Ho, H.; Singh, H.; Aljofan, M.; Nie, G. 'A high-throughput in vitro model of human embryo attachment' (2012) Fertility & Sterility vol. 97, Issue 4, p. 974-978.
Sato, T.; Stange, D. E.; Ferrante, M.; Vries, R. G. J.; Van Es, J. H.; Van Den Brink, S.; Van Houdt, W. J.; Pronk, A.; Van Gorp, J.; Siersema, P. D.; Clevers, H. 'Long-term expansion of epithelial organoids from human colon, adenoma, adenocarcinoma, and Barrett's epithelium.' (2011) Gastroenterology, 141, p. 1762-1772.
Choongkittaworn, N.; Hosick, H. L.; Jones, W. "In vitro replication potential of serially passaged mammary parenchyma from mice with different reproductive histories." Mech. of Ageing and Development (1987) 39, p. 147-175.
Dontu, G.; Abdallah, W. M.; Foley, J. M.; Jackson, K. W.; Clarke, M. F.; Kawamura, M. J.; Wicha, M. S. "In vitro propagation and transcriptional profiling of human mammary stem/progenitor cells." Genes & Development (1003) 17, p. 1253-1270.
Kim, N. M.; Oberley, T. D.; Clifton, K. H. "Primary culture of flow cytometry-sorted rat mammary epithelial cell (RMEC) subpopulations in a reconstituted basement membrane, Matrigel." Experimental Cell Res. (1993) 209, 6-20.
Chromiak, J. A.; Shansky, J.; Perrone, C.; Vandenburgh H. H. "Bioreactor perfusion system for the long-term maintenance of tissue-engineered skeletal muscle organoids." In vitro Cell Dev. Biol.—Animal (1998) 34, p. 694-703.

(Continued)

*Primary Examiner* — Nghi V Nguyen
(74) *Attorney, Agent, or Firm* — Patent Law Works LLP

(57) ABSTRACT

The present invention provides a method for culturing organoids, the method comprising: a) disassociating unprocessed organoids to produce a cell suspension; b) sieving the cell suspension through a cell strainer to retain a sieved cell suspension containing cells of about 10 μm to about 1 mm in diameter; and c) seeding cells of the sieved cell suspension into a bioreactor in a cell culture medium comprising an extracellular support matrix.

12 Claims, 4 Drawing Sheets

(56) References Cited

OTHER PUBLICATIONS

Sato, T.; Vries, R. G.; Snippert, H. J.; Wteriong M. van de.; Barker, N.; Stange, D. E.; Van ES, J. H.; Abo, A.; Kulaja, P.; Peters, P. J.; Clevers, H. "Single Lgr5 stem cells build crypt-villus structures in vitro without a mesenchymal niche." Nature Letters (2009) 459 p. 262-266.

Extended European Search Report fro Application No. 22156785.2-1118 dated Aug. 12, 2022.

Qian, Xuyu et al., Brain Region-specific Organoids Using Mini-bioreactors for Modeling ZIKV Exposure, Author Manuscript, May 19, 2016, 32 pgs., Cell. May 19, 2016; 165(5): 1238-1254. doi:10.1016/j.cell.2016.04.032.

Office Action issued by Canadian Intellectual Property Office, mailed Apr. 18, 2024, 3 pgs.

\* cited by examiner

A

B

METHODS FOR CULTURING ORGANOIDS

PRIOR RELATED APPLICATIONS

This application is a continuation of Ser. No. 16/316,573 (filed Jan. 9, 2019, now U.S. Pat. No. 11,401,501), which is a national phase filing of PCT/GB2017/052026 (filed Jul. 11, 2017) which claims priority to foreign application GB1611982.8 (filed Jul. 11, 2016), each of which is expressly incorporated by reference herein.

FILED OF INVENTION

The present invention relates to a method for culturing organoids.

BACKGROUND TO THE INVENTION

Prior to testing new drug candidates in vivo on animals or humans, in vitro testing is usually carried using either primary cell cultures or cell lines. However, results from this testing can be unreliable as the cell cultures do not mimic an in vivo system very well. This can lead to some good drugs being rejected at the in vitro stages and some poor drugs may be progressed to in vivo trials.

Organoids are three-dimensional structures of heterogeneous tissue that function like an in vivo tissue. In other words, these three-dimensional structures of tissue mimic an organ better than a traditional cell culture monolayer. Organoids therefore provide an opportunity to create cellular models of disease, which can be studied to better understand the causes of disease and identify possible treatments.

Organoids are often generated from stem cells, which can be differentiated into cerebral, renal, cardiovascular, and other types of organoids. Organoid technology has also been used to create a model of human colon cancer progression. These organoids may be created from normal intestinal cells mutated to transform into cancer cells, or may be derived from tumour cells per se. Organoids created from tumours have been shown to be a good reflection of the original tumour, providing opportunities for improved in vitro drug testing.

However, to date organoids have only been cultured in laboratory settings, which rely heavily on the technical skill of the technician involved and produce small numbers of organoids. Organoids are therefore not readily available in large numbers for drug testing. Furthermore, due to the reliance on technical skill in their culture there is little standardisation between cultures, meaning that testing carried out on different batches of organoids may not be directly comparable.

There is therefore a need to produce organoids in larger numbers and to produce organoids of consistent form and function. This will enable wider use of organoids in drug testing and improve the comparability of test results.

SUMMARY OF THE INVENTION

Accordingly, the present invention provides a method for culturing organoids, the method comprising a) disassociating unprocessed organoids to produce a cell suspension; b) sieving the cell suspension through at least one cell strainer to retain a sieved cell suspension containing cells of about 10 µm to about 1 mm in diameter; and c) seeding cells of the sieved cell suspension into a bioreactor in a cell culture medium comprising an extracellular support matrix. Sieving the cell suspension provides a particular advantage in that the size range of the sieved cells can be controlled. For example, selecting a narrow size range of cells for seeding in the cell culture medium from actively growing cells leads to the culture of homogenous organoids having a consistent size/surface area to volume ratio, resulting in reduced variability and improved quality. Without being bound by theory, it is believed that the size of the cells/organoids can be optimised to ensure that all organoids have good contact with the extracellular support matrix, as well as good nutrient access and $O_2$ tension. This ensures that all cells of the organoids develop appropriately and are of high quality, meaning that larger numbers of organoids are available for various applications, such as drug screening.

DESCRIPTION

The term organoid simply means resembling an organ. Organoids are typically defined by three characteristics: self-organization, multicellularity and functionality (Lancaster and Knoblich). Thus, the cells arrange themselves in vitro into the 3-dimensional (3D) organization that is characteristic for the organ in vivo, the resulting structure consists of multiple cell types found in that particular organ and the cells execute at least some of the functions that they normally carry out in that organ. For example, a prototypical organoid, the mouse intestinal organoid, grows as a single-layered epithelium organized into domains such that it resembles the in vivo intestinal crypt-villus architecture, comprising the different cell types of the intestine (enterocytes, goblet cells, Paneth cells, enteroendocrine cells and stem cells) and surrounding a cystic lumen (Sato et al).

As used herein, unprocessed organoids refer to organoids prepared from primary cultures of tissue samples that have not been subjected to any sieving or sizing steps during their culture period. Unprocessed organoids may be isolated from tissue samples including normal and tumour biopsies of tissues including the alimentary canal, the breast, prostate, lung, liver, ovary, pancreas, skin, kidney, brain and testis.

According to the present invention, unprocessed organoids are disassociated to break them up into (mainly) single cells. After passing through a sieve, larger clumps remain on the filter. The filtrate (i.e. the sieved cell suspension) may contain mostly single cells and/or small clumps of two or more cells, which may be from about 10 µm to about 1 mm in diameter, preferably about 10 µm to about 200 µm in diameter, more preferably about 10 µm to about 60 µm in diameter. These are then seeded in a cell culture medium comprising an extracellular support matrix. Upon further growth in culture, the viable cells divide and become multicellular organoids (referred to herein as stage I organoids). These can be "recovered" whole, from the extracellular support matrix and passed through sieves of various sizes to extract the organoids of the desired range of sizes from about 20 µm to about 200 µm (stage II organoids) as described below.

Dissociating the unprocessed organoids may refer to the process of cell dissociation using trypsin, a proteolytic enzyme which cleaves proteins, to dissociate adherent cells from each other and/or a vessel in which they are being cultured. When added to a cell culture, trypsin breaks down the proteins which enable the cells to adhere to the vessel. Trypsinization is often used to passage cells to a new vessel. As an alternative or complementary dissociation technique, chelation agents including EDTA can be used to break cell-cell junctions.

Cell culture media are well known in the art and will be familiar to the skilled person. Typically, cell culture medium comprises amino acids, salts, glucose, and vitamins and may also comprise iron and phenol red. A culture medium suitable for use in the present invention may be generated by modification of an existing cell culture medium. For example, the cell culture medium may be Dulbecco's modified Eagle medium (DMEM) and may comprise one or more additional components such as a nutrient mixture (e.g. Ham's F12), antibiotics/antifungals (e.g. penicillin/streptomycin), buffer (e.g. HEPES), glutamine, and n-Acetyl cysteine. The cell culture medium may additionally comprise a serum-free supplement, such as N2 Supplement and/or B27 Supplement.

The cell culture medium may comprise about 1% to about 99% v/v of the extracellular support matrix, preferably about 5% to about 85% v/v or about 10% to about 85% v/v of the extra cellular support matrix. In preferred embodiments of the invention the cell culture medium may comprise about 85% v/v of the extracellular support matrix. Reducing the content of extracellular support matrix in the cell culture medium can provide particular cost advantages over the prior art where it is typical to use 100% extracellular matrix. Surprisingly, the present inventors have found that the extracellular matrix content can be reduced in the method of the invention without compromising organoid growth.

Preferably, the extracellular support matrix is a gel-based extracellular matrix, which may be synthetic or naturally occurring. Additionally or alternatively, the extracellular support matrix may be a solubilized basement membrane preparation. For example, suitable basement membrane preparations may be extracted from the Engelbreth-Holm-Swarm (EHS) mouse sarcoma, a tumour rich in such extracellular matrix proteins as laminin, collagen IV, heparin sulphate proteoglycans, entactin/nidogen, and a number of growth factors. Preferably, the extracellular support matrix comprises at least two distinct glycoproteins, such as two different types of collagen or a collagen and laminin. In embodiments of the invention the extracellular support matrix may be MATRIGEL™ (which comprises laminin, entactin and collagen IV) or CULTREX™ BME (which comprises laminin, entactin, collagen IV and heparin sulphate proteoglycan). Preferably the extracellular support matrix is MATRIGEL™. Alternatively, the extracellular support matrix may be a synthetic matrix comprising peptides based on sequences present in fibronectin, collagen and/or laminin.

The culture medium may be placed on top of the extracellular support matrix and can be removed and replenished as required. In embodiments of the invention the bioreactor provides a continuous flow of culture medium, thereby continuously feeding the organoids. The composition of the culture medium may be adjusted over time in order to maximise uniform growth of the organoids.

The cell suspension obtained following disassociation of the unprocessed organoids is sieved through a cell strainer to retain a sieved cell suspension as described above. The cells of the sieved cell suspension may be single cells or may be two or more cells joined to form an organoid. The size of the cells or organoids of the sieved cell suspension can be controlled by the mesh size of the cell strainer. For example, the cell strainer may have a mesh size of about to 10 µm to about 1 mm or about 10 µm to about 500 µm. Preferably the cell strainer has a mesh size of about 20 µm to about 100 µm, more preferably about 30 µm to about 50 µm. In embodiments of the invention the cell strainer may have a mesh size of about 40 µm if mainly single cells are required in the sieved cell suspension. Suitable cell strainers will be familiar to the skilled person and include PLURISTRAINERS™.

Following sieving of the unprocessed organoids the sieved cell suspension is preferably seeded into a bioreactor. Traditional (2-dimensional) cell culture typically involves plating isolated cells on a flat surface (such as a Petri dish or tissue culture treated flask) and supplementing the cells with nutrient media. Cells are typically stored statically at 37° C. with exposure to 5% $CO_2$. In contrast, bioreactors allow 3-dimensional cell-cell and cell-matrix interactions, as well as providing spatial and temporal gradients of biochemical and physical signals, and systemic regulation including cross-talk between different organ systems. Bioreactors thereby allow cells to be differentiated into 3-dimensional tissue structures, such as organoids. A key feature of bioreactors is that they provide a dynamic culture system, rather than the static culture systems of traditional cell culture. In static cultures mass transport is based on diffusion, and generally limits tissue development to thicknesses less than 0.2 mm due to drops in oxygen tension and increased concentrations of toxic metabolites. In contrast, bioreactors provide dynamic mass transport, which allows tissue development on a millimeter to centimetre scale.

In embodiments of the invention the bioreactor may be a fed-batch bioreactor or a perfusion bioreactor, both of which create flow of culture medium to improve nutrient diffusion. Fed-batch bioreactors are typically supplied with a discrete amount of culture medium that is usually changed at intervals of days. Fed-batch bioreactors can include stirred flask bioreactors or rotating wall bioreactors, both of which provide convective flow of medium to enhance nutrient distribution. Stirred flask bioreactors typically use a magnetic stirrer bar to create a convective flow allowing continuous mixing of the medium. Rotating wall bioreactors provide a dynamic laminar flow of medium. In preferred embodiments of the invention the bioreactor is a perfusion bioreactor. Perfusion bioreactors use a pump system that can perfuse media though cells or tissue in a continuous or non-continuous manner. In perfusion bioreactor systems oxygen and nutrients are supplied to the construct interior by both diffusion and convection. The flow rate can be optimized with respect to the limiting nutrient, which is mostly oxygen due to its low solubility in culture medium. Perfusion bioreactors can provide a continuous flow of nutrients to the organoids, which the inventors have found to lead to improved organoid growth.

Perfusion bioreactors can include fed-plate bioreactors or fluidised bed bioreactors. Fed-plate bioreactors will be familiar to the skilled person and typically comprise a disposable dish typically formed from plastic, with a lid that has inlet port(s) on one side and outlet port(s) on the opposite side through which media is continuously passed. A gel-based extracellular matrix typically covers the base of the dish and contains the organoids. Fed-plate bioreactors can provide a constant flow of nutrients to the organoids, which the inventors have found to lead to improved organoid growth. Without being bound by theory, the inventors believe that use of a fed-plate bioreactor allows the organoids to be cultured with less extracellular matrix than is conventionally used in the art. The bioreactors can additionally lead to improved efficiency of the culture process and also provide cost advantages.

The fed-plate bioreactor is preferably a shallow reactor, such as a flat-bed bioreactor. The bioreactor may be from 1 m×1 m, or smaller, such as a 150 mm or 100 mm flat-bed bioreactor. In embodiments of the invention smaller vessels such as a 6-well multi-well plates may be used. Alternatively, several bioreactors may be connected in parallel or in series and may be stacked to provide arrays of fed-plate bioreactors in parallel. For example, the fed-plate bioreactor may comprise an array of bioreactors stacked on top of one another such that they are fed in parallel by the same by the same pumps delivering the same media.

In embodiments of the invention the bioreactor can provide continuous flow of nutrients to the organoids. The nutrients are typically provided in the form of a liquid feed, such as a cell culture medium, e.g. as described above, and the concentration of components of the medium can be increased or decreased over time to maximise uniform growth of the organoids. For example, it is possible to continuously feed at various dilution rates from a constant concentration liquid or constantly feed from a variable concentration feed. In alternative embodiments of the invention, nutrients may be pulse fed meaning that doses of liquid feed or other components can be added to the bioreactor in discrete amounts, but at a regular frequency. For example, pulse feeding may comprise administering a discrete amount of liquid feed or culture medium at intervals of 1 minute or 1 hour or 1 day.

Cells of the sieved cell suspension may be seeded into the bioreactor at a concentration of about 20,000 cells/ml to about 10,000,000 cells/ml, preferably about 200,000 cells/ml to about 800,000 cells/ml, more preferably about 400,000 cells/ml to about 600,000 cells/ml. The cells may be seeded into cell culture medium comprising extracellular support matrix as described herein. The cell culture medium may additionally comprise one or more kinase inhibitors, such as a Rho-associated protein kinase (ROCK) inhibitor. Such inhibitors may enhance the recovery and growth of the seeded cells. Kinase inhibitors may be present at concentrations of from about 0.1 µM to about 100 µM, preferably about 1 µM to about 20 µM. In embodiments of the invention the cell culture medium may comprise a kinase inhibitor at a concentration of about 10 µM.

Following seeding of the sieved cell suspension the cells are preferably cultured in the bioreactor to form stage I organoids. Preferably at least 100,000 or at least 250,000 stage I organoids are generated. In embodiments of the invention around 500,000 stage I organoids may be generated. However, the number of stage I organoids generated could be around 1,000,000 or around 5,000,000 or around 10,000,000 or more. The organoids may be cultured for periods of not less than 24 hours or not less than 36 hours. In embodiments of the invention the organoids may be cultured for periods of from about 24 to about 96 hours, preferably from about 36 to about 72 hours. In preferred embodiments of the invention the organoids are cultured for about 48 hours.

Stage I organoids may be recovered from the bioreactor by transferring the cell culture medium/extracellular matrix mixture to a centrifuge tube and centrifuging the tube to retain a gel layer formed by the extracellular matrix. The gel layer may then be incubated with cell recovery solution and centrifuged to form an organoid pellet.

Cell recovery solutions are well known in the art and will be familiar to the skilled person. The cell recovery solution acts to breakdown the extracellular support matrix to release the organoids without damage. Suitable cell recovery solutions include CORNING® Cell Recovery Solution.

Following removal of the stage I organoids from the bioreactor the organoids (which may be in the form of an organoid pellet) are preferably suspended in cell culture medium, which may comprise a nutrient mixture such as Ham's F12. The organoids may then be sieved through at least two cell strainers having different mesh sizes to obtain a suspension of stage II organoids having a diameter of about 20 µm to about 200 µm.

As mentioned above, the size of the organoids can be controlled by the mesh sizes of the cell strainers. For example, the cell strainers may have mesh sizes of about 20 µm and about 200 µm, preferably about 30 µm and about 100 µm, more preferably about 40 µm and about 85 µm. In more detail, the suspension comprising the recovered stage I organoids may be passed through a first cell strainer have a large mesh size (e.g. 85 µm) and all organoids larger than that mesh size may be discarded. The filtered contents may then be passed through a second cell strainer having a smaller mesh size than the first cell strainer (e.g. 40 µm) and all debris smaller than that mesh size may be discarded. The size of the retained stage II organoids will therefore be determined by the mesh sizes of the first and second cell strainers. In the example above, the stage II organoids will be between about 40 µm and about 85 µm in diameter.

The stage II organoids may be frozen for storage or shipping. In more detail, the stage II organoids may be resuspended in a freezing medium at a concentration of about 10,000 to about 500,000 organoids per 200 µl of freezing medium, preferably about 20,000 to about 300,000 organoids per 200 µl of freezing medium, more preferably about 50,000 to about 100,000 organoids per 200 µl of freezing medium. The suspended organoids may then be frozen at −80° C.

Freezing media will be familiar to the person skilled in the art and typically comprise a mixture of cell culture medium and dimethyl sulfoxide (DMSO), optionally also including foetal calf serum (FCS). Suitable freezing media are commercially available and include GIBCO® Recovery Cell Culture Freezing Medium.

BRIEF DESCRIPTION OF THE DRAWINGS

The invention will now be described in relation to one or more specific embodiments in which:

FIG. 3A: after 5 days organoids were fixed and stained with Hoeschst (specific for DNA, i.e. nuclei of eukaryotic cells) and phalloidin (specific for F-actin). The overall shape of organoids in untreated cultures or at low concentrations of inhibitor varied from round and cyst-like to convoluted and branched. As the concentration of inhibitor increases, cells are shed from the outer layer of the organoid, leading to a loss in complexity and a decrease in the overall size. FIG. 3B: morphometric analysis of organoid parameters confirmed the observations of toxicity. Organoid size decreases with increasing concentrations of inhibitor, while apoptotic nuclei and nuclei roundness (due to swelling before apoptosis) both increase with drug concentration.

EXAMPLE 1—COLORECTAL ORGANOID CULTURE PROTOCOL

1. Maintenance of Unprocessed Organoids

Figure 1:
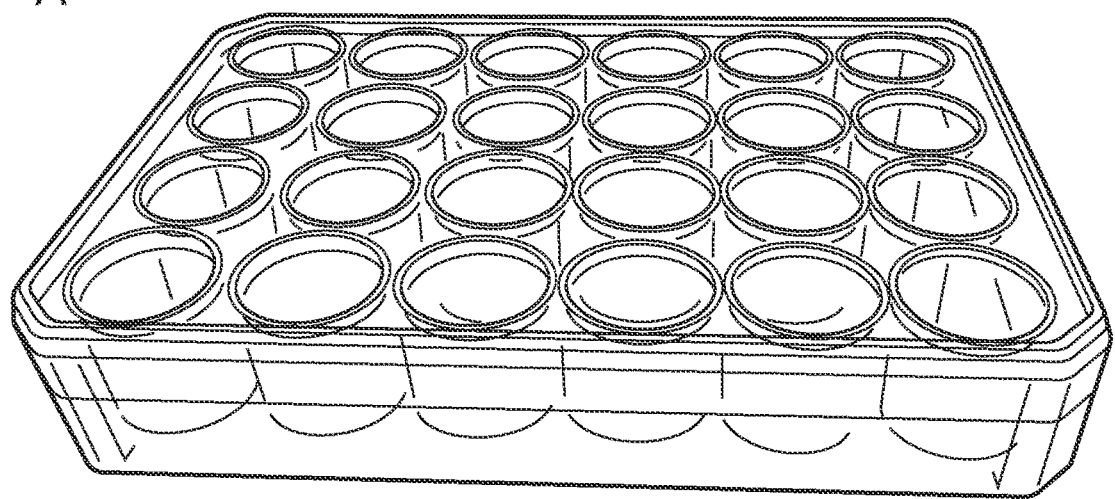
FIG. 1 shows a comparison of standard bench-scale culture of organoids and a fed-plate bioreactor of the present invention. Part A shows the 24-plate containing a total of 12 ml of cell culture medium, 1.2 ml of MATRIGEL™ and 4.8 million cells. Part B shows a 100 mm fed plate bioreactor containing 15 ml of cell culture medium, 6 ml of MATRIGEL™ or a MATRIGEL™: media mix and 2.4 million cells.
Figure 1:
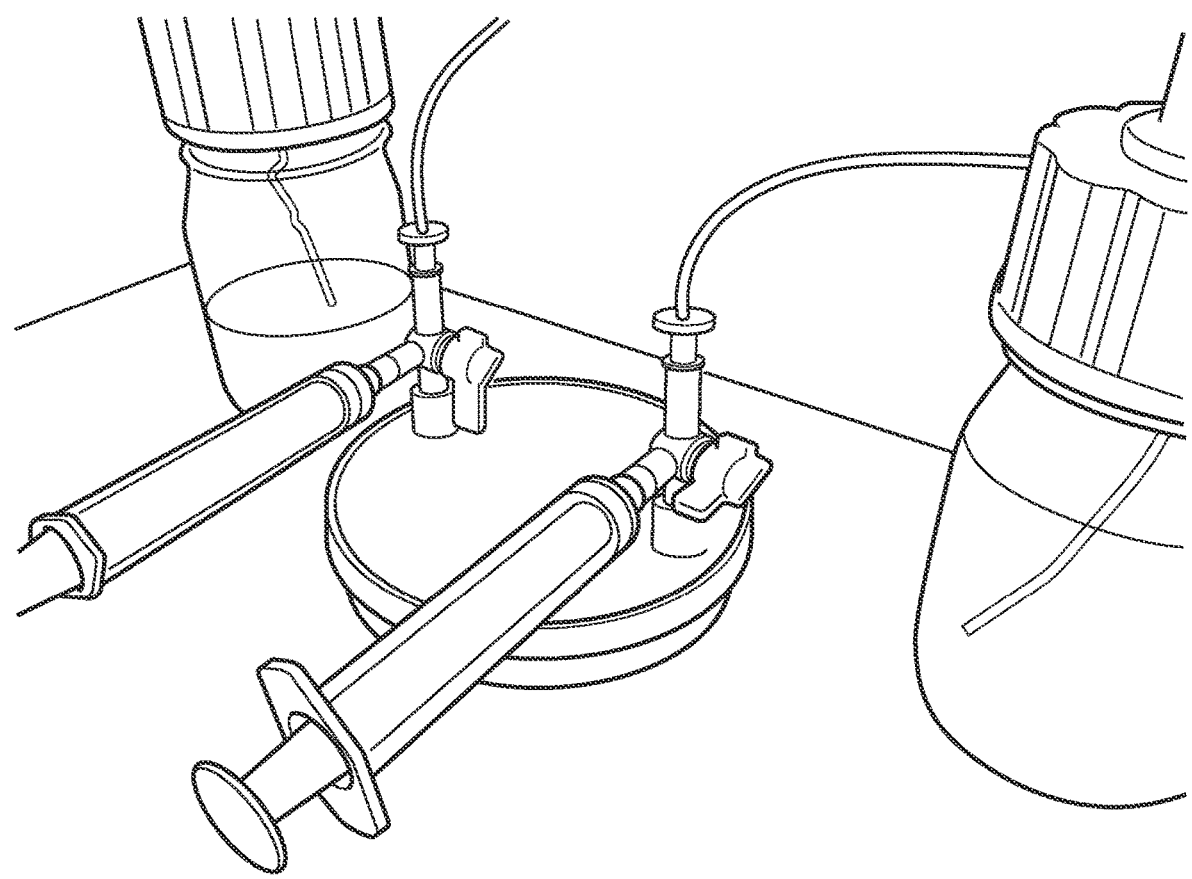

All Maintenance Protocols are performed within a Class II laminar flow cabinet to maintain sterility.

3+ Medium contains Advanced DMEM/F12 (with high glucose and pyruvate) supplemented with HEPES, 1× GLUTAMAX™, penicillin/streptomycin (100 U/mL).

6+ Medium contains Advanced DMEM/F12 (with high glucose and pyruvate) supplemented with HEPES, 1× GLUTAMAX™, penicillin/streptomycin (100 U/mL), 1×B27, 1×N2 and 1.25 mM n-Acetyl cysteine.

1.1 Manual Trituration Protocol (ISO50, ISO78)

Trituration is carried out using un-supplemented DMEM/F12 media, pre-equilibrated to 4° C. Fresh MATRIGEL™, stored in frozen aliquots, is thawed and maintained in liquefied form on ice.

The culture medium on the organoids in polymerised MATRIGEL™ in a 24-well plate is replaced with chilled media. The MATRIGEL™ domes are disrupted with the end of a 1000 µL pipette tip. The contents of no more than 3 wells are combined in 15 ml tubes, on ice. Chilled media is added, to dilute the used MATRIGEL™. Organoids are then pelleted by centrifugation at 1000 rpm for 3 minutes and the old media and MATRIGEL™ is removed by aspiration. The pelleted organoids from several tubes are combined in a volume of about 400 µl media and disaggregation is carried out by passing them up and down at least 100 times, through a 1000 µL pipette tip. Chilled medium is added, the organoids are pelleted by centrifugation and the media is removed by aspiration, leaving a dry pellet. The required volume of fresh 100% MATRIGEL™ is added, and the mix is plated out at 50 µL per well of a 24-well plate (or as required). After polymerisation of the MATRIGEL™ at room temperature for at least 15 minutes, 500 µL of "6+" crypt culture medium is added to each well and the plate is cultured in a humidified incubator at 37° C. and 5% $CO_2$. The media is changed every 2-3 days until the organoids grow too large or dense for the MATRIGEL™ and require repeat disaggregation by trypsinisation or trituration.

1.2 Trypsinisation (ISO72)

Trypsinisation procedures are carried out using un-supplemented DMEM/F12 media and TRYPLE™ pre-equilibrated to room temperature. Fresh MATRIGEL™, kept in frozen aliquots, is thawed and maintained in liquefied form on ice.

Organoids in MATRIGEL™ are washed in PBS and then incubated for 3 minutes in TRYPLE™ (250 µL per 50 µL MATRIGEL™ dome) at 37° C. The reaction is stopped by inhibiting the enzyme with an equal volume of DMEM/F12+10% FBS or Defined Trypsin Inhibitor (INVITROGEN®). The MATRIGEL™ and media mixture is pipetted up and down 10-20 times through a 1000 µL pipette tip to assist disaggregation. The contents of up to 3 wells are combined in 15 ml conical bottomed tubes. DMEM/F12 media is added, to dilute the used MATRIGEL™, which is aspirated following centrifugation at 1000 rpm for 3 minutes. The required volume of 100% MATRIGEL™ is added to the dry organoid pellet and the mix is plated out at 50 µL per well of a 24-well plate (or as required). After polymerisation of the MATRIGEL™ at room temperature for at least 15 minutes, 500 µL of "6+" crypt culture medium is added to each well and the plate is cultured in a humidified incubator at 37° C. and 5% $CO_2$. The media is changed every 2-3 days until the organoids grow too large or dense for the MATRIGEL™ and require repeat disaggregation by trypsinisation or trituration.

2. Bioprocessor Protocols

FIG. 1B shows a 100 mm flatbed bioreactor and a comparison of the same with a 24 well plate (FIG. 1A).

2.1 the Bioprocessor

Bioprocessing is the process by which organoids are cultured in a 100 mm dish, in a "flat-bed" bioreactor and then separated into different sizes by fractionation (see section 4) using 85 µm and 40 µm PLURISTRAINERS™ to obtain organoids of the desired dimensions.

The 100 mm dish flat-bed bioreactor, has a lid, specially adapted with inlet and outlet valves to facilitate addition to and aspiration of media from the surface of the organoid/MATRIGEL™ mix contained within the dish. Fresh growth media is contained within a "feed reservoir" bottle with an attached HEPA filter and dip tube. An identical bottle is the waste reservoir. Tubing to these bottles is adjoined to pump manifold tubes and attached to a peristaltic pump by tube clips, as appropriate to allow fresh media to be pumped from the media bottle onto the MATRIGEL™ surface, or waste media to be removed to the waste reservoir. Hence, the system is termed a "Fed-plate" bioreactor as the media exchange does not need manual intervention.

2.2 Seeding a "Fed-Plate" Bioreactor (ISO50)

All parts of the bioreactor are sterile. Parts are autoclaved or otherwise sterilised by soaking in 70% alcohol, as necessary. 6+ growth media, pre-warmed to 37° C. is placed in the "feed" reservoir.

Organoids are trypsinised by incubation with TRYPLE™ according to the protocol above (1.2 Trypsinisation). Following aspiration of the old MATRIGEL™ from the combined, trypsinised organoids, the pellet is re-suspended in 10 mL chilled DMEM/F12 and passed through a 40 µm cell strainer. The resulting filtrate consists mainly of single cells. (The larger aggregates caught in the strainer can be harvested and used if required.) A 100 mm culture dish is seeded with 400,000-600,000 cells/mL in a total volume of 6 mL of 100% MATRIGEL™ or a MATRIGEL™: 6+ media mix (from 2% to 99.9% MATRIGEL™). Following polymerisation of the MATRIGEL™ at room temperature or 37° C., 15 mL 6+ growth medium containing ROCK inhibitor is added. The plate is incubated for 24 hours under static conditions.

2.3 Using the Bioprocessor

The lid of the 100 mm dish containing the cells seeded in MATRIGEL™ (see 2.1 Seeding a "fed-plate" bioreactor) is replaced with the sterile, "fed-plate" bioreactor lid. The bioreactor, media bottles and associated tubing are maintained in a humidified incubator at 37° C. and 5% $CO_2$ with the pump at 0.9 rpm maintaining a flow rate of 0.59 ml/hr. Organoids are normally cultured for 48 hours prior to recovery, fractionation and freezing (see protocols below).

3. Recovery of Whole Organoids from MATRIGEL™ (or MATRIGEL™/Media Mix)

Sterility should be maintained throughout this process.

The MATRIGEL™/Organoid layer is washed with PBS. 10 ml chilled "Cell Recovery" solution (Invitrogen) is added and the MATRIGEL™ layer is disrupted with the end of a 1000 mL tip. The plate is incubated on ice for 25 min with gentle agitation. The contents of the dish are then placed in a 50 mL tube and made up to 50 mL with DMEM/F12. The organoids are pelleted by centrifugation at 1000 rpm for 3 min. or until an organoid pellet is visible. The used MATRI- GEL™/media mix is aspirated and the organoids are re-suspended in 5-10 mL of DMEM/F12 prior to fractionation.

4. Fractionation (Sizing Protocol)

Figure 2:
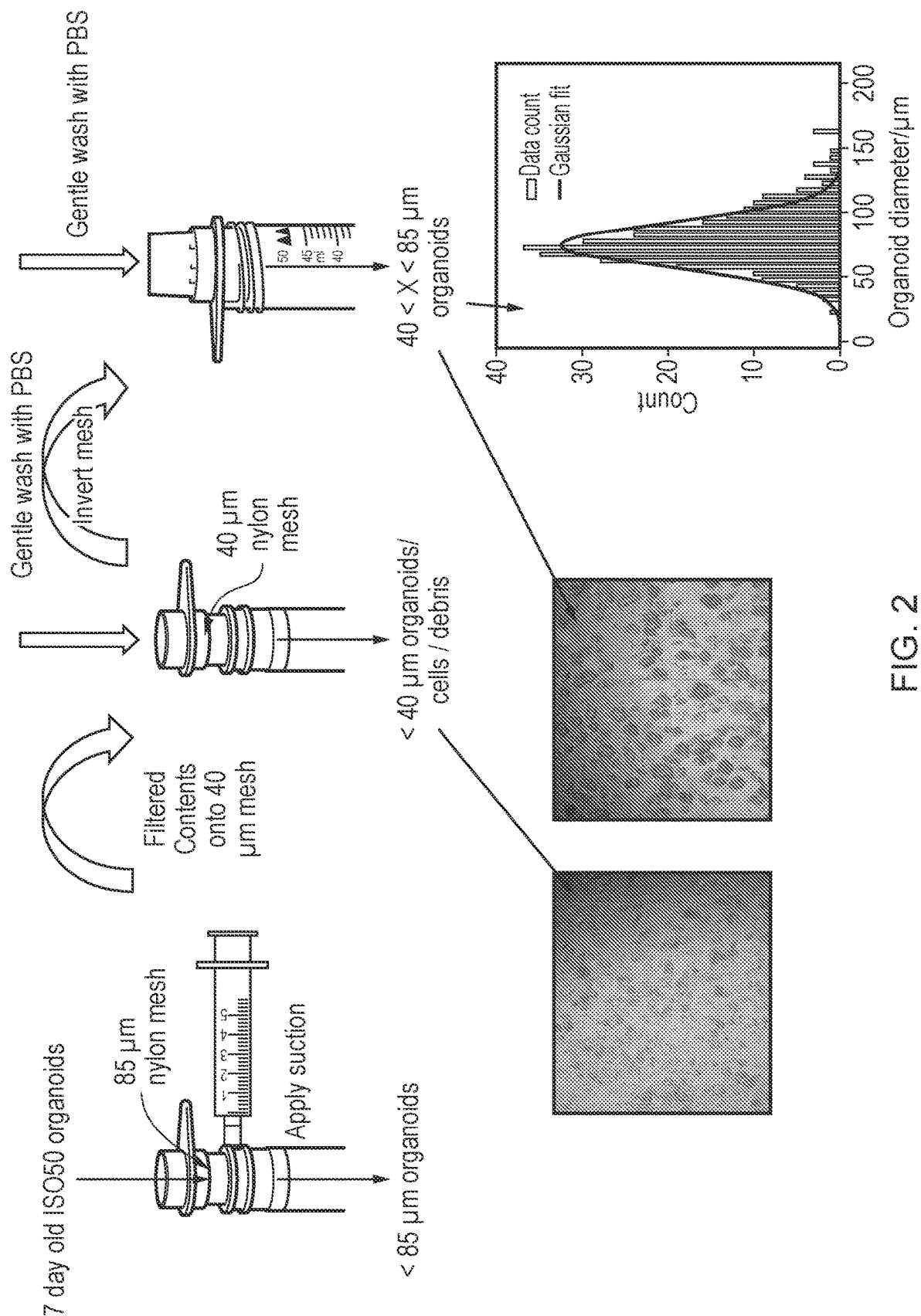
FIG. 2 shows a schematic illustration of the fractionation process in which stage I organoids are sieved through two cell strainers of different mesh sizes to obtain a suspension of stage II organoids. The lower right-hand panel illustrates the size distribution of the stage II organoids obtained using cell strainers with mesh sizes of 85 µm and 40 µm.

The "recovered" organoid suspension (see previous section) is passed sequentially through cell strainers, to retrieve organoids of the required dimensions. The schematic (FIG. 2) shows the process with 85 µm and 40 µm strainers. An estimate of the numbers and size of the organoids is obtained in each fraction using the BECKMAN COULTER® MS3, using ISOTON® II buffer with 40% glycerol and a 400 µm aperture. A small fraction of the filtrates is trypsinised to single-cell using TRYPLE™ and counted to give an estimate of the total number of cells within the organoids and thus an average cell count per organoid.

5. Freezing Protocol for Seeding Organoids into a 384-Well Plate

The organoids pelleted by centrifugation and re-suspended in commercial freezing mixture such that there are 500,000 organoids per mL, 200 µL per cryovial (100,000 organoids). The cryovials are transferred to a "Mr Frosty" container and placed at −80° C. freezer for at least 24 hours. The vials can then be transferred to other containers and stored long-term at −80° C.

EXAMPLE 2—COLORECTAL ORGANOID VALIDATION

Drug Titration Assay Results

ISO50 (Isolation number 50) colorectal cancer organoids were cultured in a fed-plate bioreactor for 3 days, recovered from the MATRIGEL™ and stored frozen at −80° C. They were subsequently revived and used to seed a 384-well plate at a density of 350 organoids per well in 12 µl MATRIGEL™. The organoids were fed with 25 µl growth medium containing 0-2.5 µM MK1775, a WEE1 inhibitor (8 replicates). After 5 days, the organoids were fixed and stained with Hoechst (blue fluorescent stain specific for DNA i.e. nuclei of eukaryotic cells) and phalloidin (pink stain for F-actin).

Figure 3A:
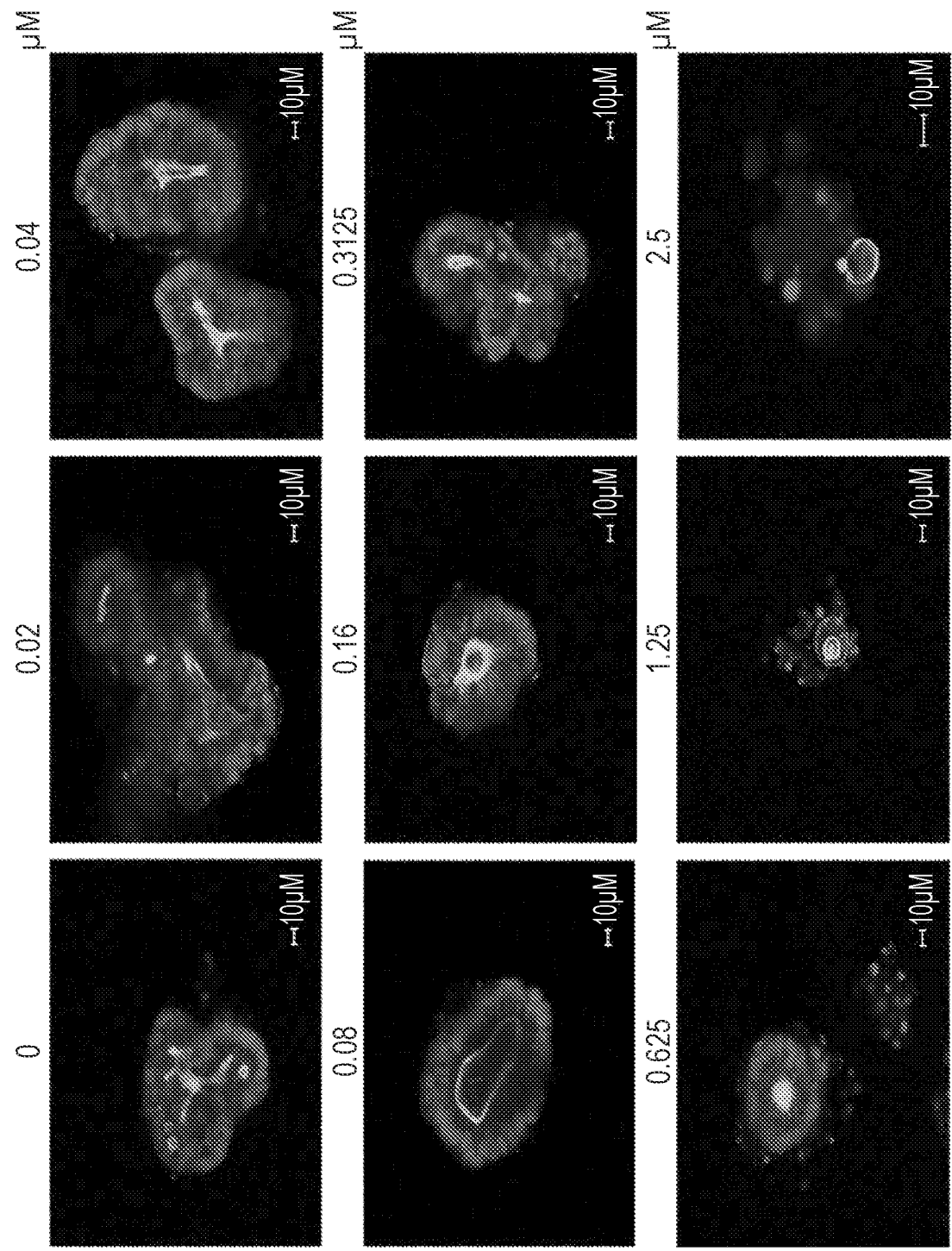
FIG. 3A and FIG. 3B show the effect of WEE1 inhibitor on organoids cultured using a fed-plate bioreactor according to the present invention. Cultured organoids were fed with 25 µl of growth medium containing 1 to 2.5 µM MK1775, a WEE1 inhibitor (8 replicates).

Confocal imaging shows the blue nuclei of cells with pink-stained actin filaments (see FIG. 3A). The actin filaments are spread throughout the structures, but are more concentrated in the lumen, in the centre of the organoid. Representative organoids are pictured from selected wells at each concentration. The overall shape of organoids in an untreated culture, or at low concentrations of inhibitor, can vary from round and cyst-like to convoluted and branched. As the concentration of inhibitor increases, cells are shed from the outer layer of the organoid, leading to a loss of complexity and a decrease in the overall size.

Figure 3B:
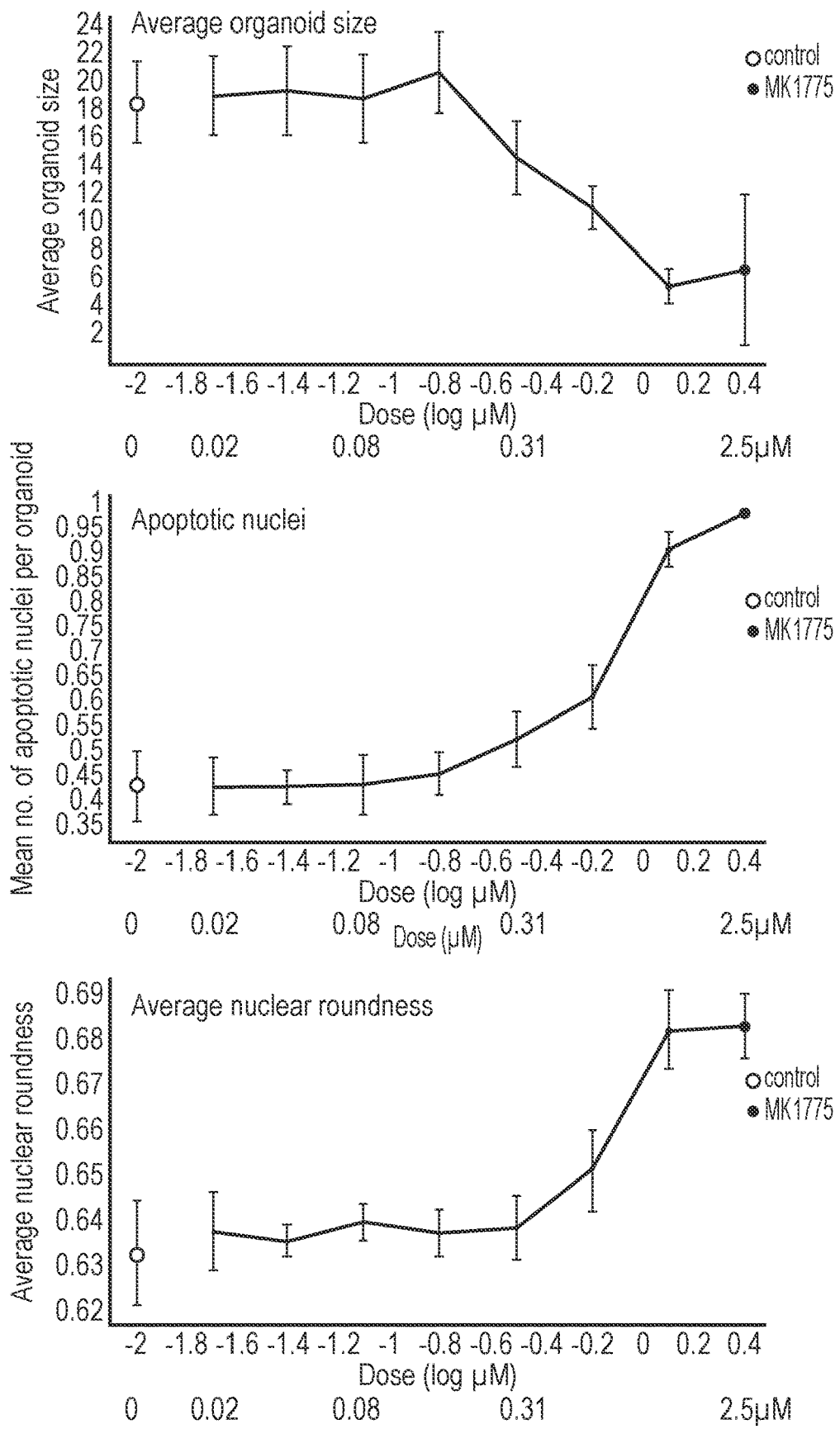

Morphometric analysis of over 1000 parameters of the organoids confirmed the observations of toxicity. Example graphs are shown in FIG. 3B. Organoid size decreases with increasing concentrations of inhibitor. Apoptotic nuclei and nuclei roundness (due to swelling before apoptosis), both increase with drug concentration.

Each of the following references is incorporated by reference in its entirety for all purposes.

Lancaster, M. A.; Knoblich, J. A. (2014) "Organogenesis in a dish: modeling development and disease using organoid technologies." Science 345:1247125-1247125.

Sato, T.; Vries, R. G.; Snippert, H. J.; van de Wetering, M.; Barker, N.; Stange, D. E.; van Es, J. H.; Abo, A.; Kujala, P.; Peters, P. J.; Clevers, H. (2009) "Single Lgr5 stem cells build crypt villus structures in vitro without a mesenchymal niche." Nature 459:262-265.

The invention claimed is:

1. A method for processing organoids, the method comprising:
   culturing unprocessed organoids; and
   disassociating the cultured unprocessed organoids to produce a cell suspension;
   sieving the cell suspension through a cell strainer to obtain a sieved cell suspension containing cells of about 10 µm to about 1 mm in diameter; and
   seeding cells of the sieved cell suspension into a bioreactor in a cell culture medium comprising an extracellular support matrix; and
   recovering stage I organoids from the bioreactor;
   wherein the bioreactor is a fed-plate bioreactor.

2. The method of claim 1, wherein the fed-plate bioreactor is a flat-bed bioreactor.

3. The method of claim 1, wherein the bioreactor is a perfusion bioreactor.

4. The method of claim 1, wherein the fed-plate bioreactor comprises an arrangement of bioreactors that are fed in parallel or in series.

5. The method of claim 1, wherein the cell culture medium comprises about 1% to about 99% v/v of the extracellular support matrix.

6. The method of claim 5, wherein the cell culture medium comprises about 5% to about 85% v/v of the extracellular support matrix.

7. The method of claim 1, wherein the extracellular support matrix is a solubilized basement membrane preparation.

8. The method of claim 1, wherein the extracellular support matrix comprises laminin, entactin and collagen IV, or comprises laminin, entactin, collagen IV and heparin sulphate proteoglycan.

9. The method of claim 1, wherein the cell strainer has a mesh size of about 30 µm to about 50 µm.

10. A method for processing organoids, the method comprising:
    culturing unprocessed organoids;
    disassociating the cultured unprocessed organoids to produce a cell suspension;
    sieving the cell suspension through a cell strainer having a mesh size of about 30 µm to about 50 µm to obtain a sieved cell suspension; and
    seeding cells of the sieved cell suspension into a bioreactor in a cell culture medium comprising an extracellular support matrix; and
    recovering stage I organoids from the bioreactor.

11. The method according to claim 10, wherein the bioreactor is a fed-plate bioreactor.

12. The method according to claim 10, wherein the cell strainer has a mesh size of about 40 µm.

* * * * *